United States Patent
Feygin

(10) Patent No.: US 7,579,194 B2
(45) Date of Patent: Aug. 25, 2009

(54) APPARATUS AND METHOD FOR INVESTIGATING CHEMICAL ENTITIES

(75) Inventor: Ilya Feygin, Mountainside, NJ (US)

(73) Assignee: TechElan, LLC, Mountainside, NJ (US)

( * ) Notice: Subject to any disclaimer, the term of this patent is extended or adjusted under 35 U.S.C. 154(b) by 868 days.

(21) Appl. No.: 10/769,220

(22) Filed: Jan. 30, 2004

(65) Prior Publication Data

US 2004/0184961 A1 Sep. 23, 2004

Related U.S. Application Data

(60) Provisional application No. 60/443,824, filed on Jan. 30, 2003.

(51) Int. Cl.
*G01N 21/00* (2006.01)
(52) U.S. Cl. .................................... 436/164
(58) Field of Classification Search .................. 436/164
See application file for complete search history.

(56) References Cited

U.S. PATENT DOCUMENTS

| | | | | |
|---|---|---|---|---|
| 3,368,247 A | * | 2/1968 | Orban | 24/16 R |
| 4,972,042 A | * | 11/1990 | Seabourne et al. | 174/23 R |
| 5,625,737 A | * | 4/1997 | Saito | 385/137 |
| 5,814,524 A | * | 9/1998 | Walt et al. | 436/518 |
| 5,980,120 A | * | 11/1999 | Narayanan | 385/89 |
| 6,157,442 A | * | 12/2000 | Raskas | 356/39 |
| 6,519,032 B1 | * | 2/2003 | Kuebler et al. | 356/337 |
| 6,541,271 B1 | * | 4/2003 | McFarland et al. | 436/171 |

OTHER PUBLICATIONS

Goff, D.R. "A Brief History of Fiber Optic Reference Guide." 3rd Ed., Focal Press. Woburn Massachusetts, 2002.*

* cited by examiner

*Primary Examiner*—Walter D Griffin
*Assistant Examiner*—Bobby Ramdhanie
(74) *Attorney, Agent, or Firm*—DeMont & Breyer, LLC

(57) ABSTRACT

An apparatus and method for monitoring a large number of binding interactions and obtaining data related to the interactions. In accordance with the illustrative embodiment, the apparatus includes an IR sensor, a sliding separator, and IR-transmitting fibers that are optically coupled, at a first end thereof, to the sensor. The sliding separator adjusts the spacing between fibers as is required for interfacing the second end of the fibers with any of a variety of sample carriers. The second end of the fibers capture chemical entities form the sample carriers. The chemical entities at the end of the fibers are then contacted with a binding compound. If binding activity occurs, a thermal signal indicative thereof will be transmitted through the fiber to the sensor.

14 Claims, 3 Drawing Sheets

FIG. 5
FIG. 6
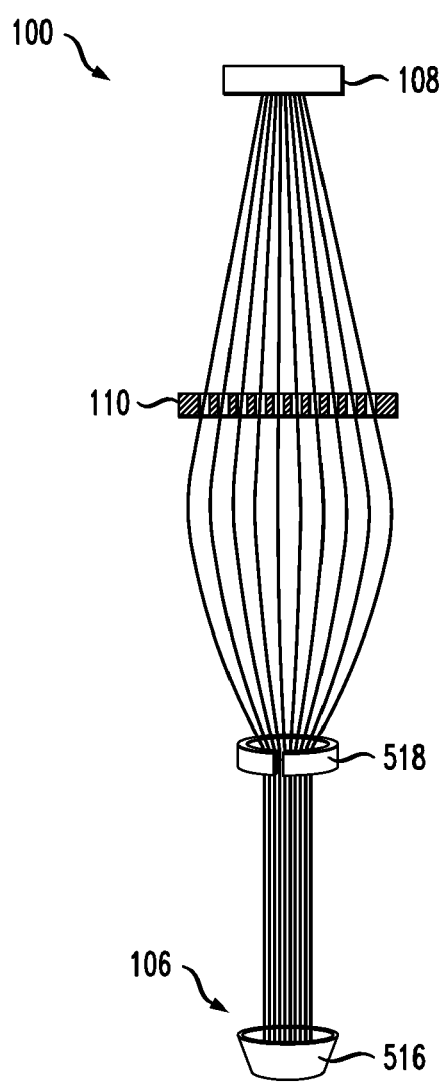
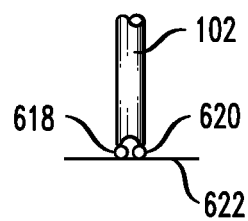

APPARATUS AND METHOD FOR INVESTIGATING CHEMICAL ENTITIES

STATEMENT F RELATED CASES

This case claims priority of U.S. provisional patent application 60/443,824, which was filed on Jan. 30, 2003, which is incorporated by reference herein.

FIELD OF THE INVENTION

The present invention relates to an apparatus and method for determining the structural parameters of unknown chemical entities through binding interactions.

BACKGROUND

The structure of a complex chemical entity (e.g., proteins) can be decoded via its binding activity with known chemical entities (e.g., small molecules). But this requires the investigation of a very large number of such interactions. Current technologies (e.g., fluorescent assays, etc.) and equipment for decoding the structure of proteins through binding require complex equipment and extensive development of assays as well as the selection of proper fluorescent labels. Other techniques, which decode structures directly (i.e., without binding) are very complex (e.g., mass spectrometers, etc.) and denature proteins in the process. As a consequence, there is a need for a relatively simple, low-cost, and high-throughput apparatus that is capable of monitoring binding interactions and obtaining the data required for identifying unknown chemical entities.

SUMMARY

Some embodiments of the present invention are capable of monitoring binding interactions and obtaining data concerning the interactions. In accordance with the illustrative embodiment, binding activity is investigation directly, through its thermal signature. As a consequence, the illustrative embodiment of the present invention is a "label-free" technology, in that it does not require special assay development and labeling.

In accordance with the illustrative embodiment, an apparatus for monitoring and obtaining data on binding interactions includes an IR sensor, a sliding separator, and IR-transmitting fibers that are optically coupled, at a first end thereof, to the sensor. The sliding separator adjusts the spacing between fibers as is required for interfacing the second end of the fibers with any of a variety of sample carriers. In some embodiments, the second end of the fibers is physically adapted to capture and immobilize chemical entities that are contained in the sample carriers.

After the chemical entities are engaged to the second end of the fibers, they are brought into contact with a binding compound. If binding activity occurs, a thermal signal indicative thereof will be transmitted through the fiber to sensor 108. Since ambient conditions are identical for all fibers, even the slightest fiber-to-fiber variations in activity will be noticeable. In some embodiments, unknown chemical entities can be identified by analysis of the thermal signals.

BRIEF DESCRIPTION OF THE DRAWINGS

FIG. 5 depicts the insertion of the second end 104 of fibers 102 into a well that contains binding compound.

FIG. 6 depicts a variation of the arrangement shown in FIG. 5, wherein second end 104 of fibers 102 are interfaced with a surface that has binding compound immobilized thereon.

DETAILED DESCRIPTION

The inventor recognized that decoding of proteins through various interactions (e.g., protein/protein, protein/small molecule-drug, protein/antibody, protein/peptide, etc.) by monitoring slight energy-level variations during binding is feasible using a ratiometric (comparative) evaluation of these events through thermal balance (i.e., infrared-radiation level).

It is very difficult to measure absolute changes in thermal-energy variations during binding. Doing so requires special calorimetric chambers. But it is possible to monitor very small differences in activity between reference "blank" sites and other unknown sites that are being subjected to investigation. This ratiometric approach is valid only if substantially all other parameters that affect the thermal balance are constant and if the events under investigation are taking place simultaneously.

The inventive device provides an opportunity for massively-parallel investigation of binding activities by monitoring thermal emission from hundreds or thousand of separate sites.

Figure 1:
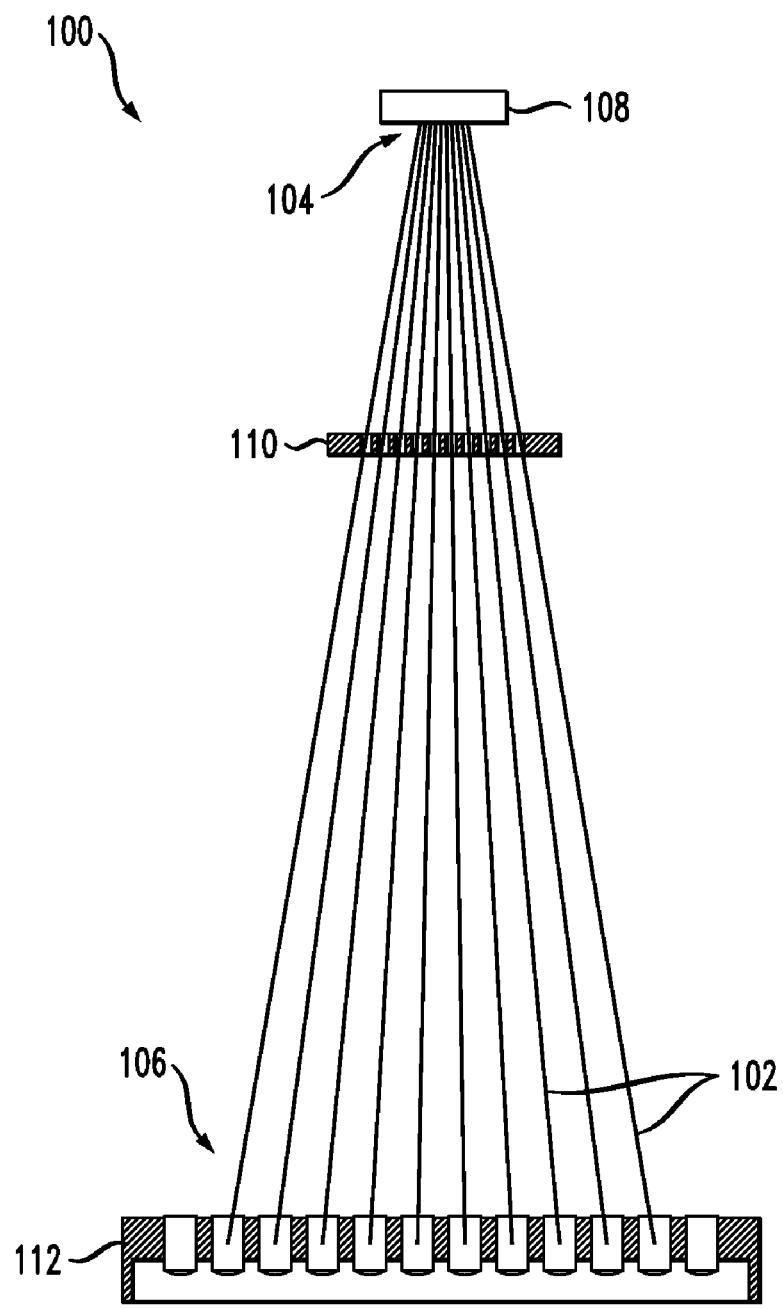
FIG. 1 depicts apparatus 100 in accordance with the illustrative embodiment of the present invention.

FIG. 1 depicts apparatus 100 for investigating binding activity in accordance with the illustrative embodiment. As depicted in FIG. 1, apparatus 100 includes a plurality of infrared-radiation ("IR")-transmitting fibers 102, sensor(s) 108, and sliding separator 110.

A variety of IR-transmitting fibers are commercially available, such as chalcogenide glass, polycrystalline IR ("PIR") fibers, and heavy metal fluoride glass ("HMFG") and suitable for use in conjunction with the illustrative embodiment of the present invention.

First end 104 of each fiber 102 is advantageously optically coupled to a dedicated sensing element (e.g., a pixel, etc.) or dedicated group of sensing elements of sensor 108. Furthermore, fibers 102 are bound or otherwise immobilized near first end 104. In some embodiments, first end 104 of each of fibers 102 is optically coupled and physically attached (e.g., via index-matching epoxy, etc.) to sensor 108. In some other embodiments, fibers 102 are immobilized near first end 104 by a suitable clamp (not depicted), etc., rather than being attached directly to sensor 108. But regardless of whether or not fibers 102 are attached to sensor 108, they are optically coupled to it.

In some embodiments, sensor 108 is a thermal-sensing element, as is known in the art. For example, the sensor can be a mercury-cadmium-telluride-based device. In some other embodiments, sensor 108 is a MOS, Bolometric, or other type of thermally-sensitive array.

To capture a chemical entity for study, second end 106 of fibers 102 is "dipped" into sample carrier 112. The dipping process can be manual or automated in known fashion. The wells in sample carrier 112 contain, in various embodiments, protein or other small molecules. Different entities, known or unknown can be present in various wells. Also, for ratiometric studies, every other well can be empty or can contain a known material for reference.

Figure 2:
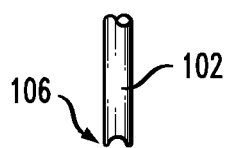
FIG. 2 depicts a physical adaptation at second end 104 of a fiber 102.

In some embodiments, the ability of second end 106 of fiber 102 to capture and immobilize a chemical entity is enhanced by one or more physical adaptations. In some embodiments, the physical adaptation is the shape of second end 106 of fiber 102, such as a concave shape, as is depicted in FIG. 2. This results in the end of the fiber retaining a predetermined amount of liquid and chemical entity. In some other embodiments, fiber 102 is equipped with a capillary intake whereby capillary action is used to retain a chemical entity. In yet some additional embodiments, the second end 106 of fiber 102 is modified by plasma treatments to render it hydrophilic or hydrophobic, as desired. These physical adaptations promote capture and immobilization of a chemical entity.

Figure 3:
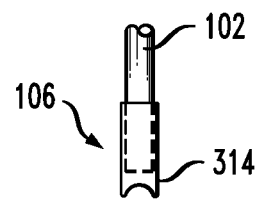
FIG. 3 depicts a removable tip for use at second end 104 of fiber 102.

As depicted in FIG. 3, in some embodiments, removable tip 314 is added to second end 104 so that the removable tip, rather than the end of the fiber is contaminated by material in the wells of sample carrier 112. In some embodiments, removable tip 314 is physically adapted to promote capture and immobilization of a chemical entity as described above.

Figure 4:
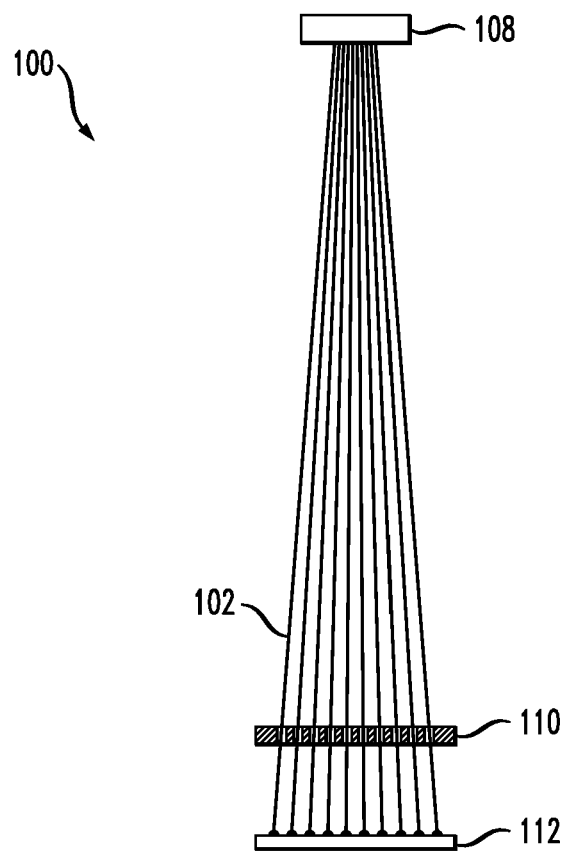
FIG. 4 depicts apparatus 100 of FIG. 1 in use with a sample carrier having more wells.

Sliding separator 110 fans out fibers 102 in a predetermined manner and pattern to fit sample carrier 112 (e.g., micro-titer plates having 96, 384, or 1536 wells, etc.) of a variety of configurations. In particular, the position of sliding separator 110 along fibers 102 determines the distance between second ends 106 of adjacent fibers 102. Assume, for example, sample carrier 112 of FIG. 1 is a 96-well micro-well plate and sample carrier 112 of FIG. 4 is a 384-well plate. The wells in a 96-well plate are spaced further apart than the wells in a 384 well plate. As a consequence, second ends 106 of adjacent fibers 102 must be further apart when used in conjunction with a 96-well plate than when used with a 384-well plate. This is accomplished by simply positioning sliding separator 110 relatively further from second end 106 of fibers 102 for use with a 96-well plate and relatively closer to second end 106 of fibers 102 for use with a 384-well plate.

Once the chemical entities are engaged to second end 106 of fibers 102, the fibers are, in some embodiments, simultaneously inserted into well 516, as depicted in FIG. 5. Simultaneous insertion is particularly desirable, if not necessary, for ratiometric studies. In some embodiments, well 516 contains a binding compound. Based on knowledge of the behavior of the binding compound with various compounds, the unknown entities obtained from sample carrier 112 can be identified. The binding compound can be a small molecule drug, an antibody, a protein, a peptide, etc.

To facilitate simultaneous insertion into well 516, apparatus 100 includes collar 518 for bundling fibers 102. In some embodiments, collar 518 is slid over fibers 102 at second end 106 after the fibers have received the chemical entities during the first "dipping" operation.

If binding activity (i.e., between a chemical entity from sample carrier 112 and the binding compound) occurs at second end 106 of any individual fiber 102, a thermal signal indicative thereof will be transmitted to sensor 108. Since ambient conditions are identical for all fibers, even the slightest fiber-to-fiber variations in activity will be noticeable.

As depicted in FIG. 6, in some embodiments, rather than dipping fibers 102 in well 516 to receive binding compound, the fibers, with chemical entity 618 attached at second end 106, are interfaced with binding chemical 620 that is immobilized or otherwise present on surface 622. The surface is advantageously IR reflective and is advantageously shaped (e.g., flat, parabolic, etc.) to direct maximum signal strength toward sensor 108.

It is to be understood that the above-described embodiments are merely illustrative of the present invention and that many variations of the above-described embodiments can be devised by those skilled in the art without departing from the scope of the invention. For example, in this specification, specific details are provided in order provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Furthermore, the particular features, structures, materials, or characteristics can be combined in any suitable manner in one or more embodiments. It is therefore intended that such variations be included within the scope of the following claims and their equivalents.

I claim:

1. An apparatus comprising:
    a plurality of IR-transmitting optical fibers, wherein said optical fibers each have a first end and a second end, and wherein said fibers are capable of transmitting infrared radiation ("IR") generated during decoding of a protein via a binding interaction of the protein with a binding compound;
    a sensor for sensing IR generated from the binding interaction, wherein said sensor is in IR-sensing contact with said first end of each of said optical fibers; and
    a sliding separator, wherein said separator engages said plurality of fibers and is slideable therealong to alter a separation therebetween, wherein the alterable separation facilitates the engagement of the optical fibers with individual samples disposed in wells of any one of a variety of different-sized sample plates having different spacing between the wells.

2. The apparatus of claim 1 further comprising a collar for bundling said optical fibers.

3. The apparatus of claim 1 wherein said second end of said optical fibers are physically adapted to receive the protein.

4. The apparatus of claim 3 wherein said individual samples comprise the protein.

5. The apparatus of claim 1 further comprising a surface having the binding compound disposed thereon.

6. The apparatus of claim 1 wherein said first end of said optical fibers are physically coupled to said sensor.

7. A method comprising:
    positioning a sliding separator along a plurality of IR-transmitting optical fibers, wherein a change in the relative position of the sliding separator along the fibers alters a separation therebetween, wherein the alterable separation facilitates the engagement of the optical fibers with individual samples disposed in wells of any one of a variety of different-sized sample plates having different spacing between the wells;
    contacting the first end of a first one of the optical fibers with a first sample within one of the wells, wherein the contact introduces a chemical entity and a binding compound to each other, thereby resulting in a first binding interaction; and conducting a first thermal signal resulting from the first binding interaction to a thermal sensor through said at first IR-transmitting optical fiber.

8. The method of claim 7 further comprising physically engaging the chemical entity to the first end of the first optical fiber before contacting the first end of the fiber with the first sample, wherein the first sample contains the binding compound.

9. The method of claim 7 further comprising physically engaging the binding compound to the first end of the first optical fiber before contacting the first end of the first fiber with the first sample, wherein the sample contains the chemical entity.

10. The method of claim 7 further comprising: contacting the first end of a second optical fiber with a second sample within another one of the wells, wherein the contact introduces a second chemical entity and the binding compound to each other, thereby resulting in a second binding interaction, wherein contact between the first optical fiber and the first sample and the second optical fiber and the second sample is simultaneous; conducting a second thermal signal resulting from the second binding interaction to a thermal sensor through said second IR-transmitting optical fiber; and comparing the first thermal signal and the second thermal signal to one another.

11. A method comprising:
  positioning a movable separator along a plurality of IR-transmitting optical fibers to obtain a desired spacing between adjacent IR-transmitting optical fibers at a sampling end thereof;
  generating a thermal signal from a binding interaction between a protein and a binding compound, wherein the thermal signal is generated proximal to the sampling end of at least one of the IR-transmitting optical fibers; and
  conducting the thermal signal through at least one of said IR-transmitting optical fibers.

12. The method of claim 11 further comprising engaging a chemical entity to said sampling end of said IR-transmitting fibers.

13. The method of claim 11 wherein conducting a thermal signal further comprises conducting said thermal signal to a thermal sensor.

14. An apparatus comprising:
  a plurality of IR-transmitting optical fibers each having a first end and a second end;
  a sensor for sensing IR, wherein the sensor is in IR-sensing contact with the first end of each of the optical fibers; and
  a sliding separator, wherein the separator engages the plurality of fibers and is slideable therealong to alter a separation therebetween, wherein the alterable separation facilitates the engagement of the optical fibers with individual samples disposed in wells of any one of a variety of different-sized sample plates having different spacing between the wells.

* * * * *

UNITED STATES PATENT AND TRADEMARK OFFICE
CERTIFICATE OF CORRECTION

| | |
|---|---|
| PATENT NO. | : 7,579,194 B2 |
| APPLICATION NO. | : 10/769220 |
| DATED | : August 25, 2009 |
| INVENTOR(S) | : Ilya Feygin |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1539 days.

Signed and Sealed this

Fourteenth Day of September, 2010

David J. Kappos
*Director of the United States Patent and Trademark Office*